United States Patent [19]

Watt

[11] 4,067,863

[45] Jan. 10, 1978

[54] BLOOD PLASMA FRACTIONATION

[76] Inventor: John G. Watt, Langlaw, Whitehill, Dalkeith, Midlothian, Scotland

[21] Appl. No.: 550,147

[22] Filed: Feb. 14, 1975

Related U.S. Application Data

[63] Continuation-in-part of Ser. No. 303,761, Nov. 6, 1972, abandoned.

[30] Foreign Application Priority Data

Mar. 28, 1969 United Kingdom ............... 16536/69

[51] Int. Cl.$^2$ ................................................ A23J 1/06
[52] U.S. Cl. .................................. 260/112 B; 260/122
[58] Field of Search ................. 260/112 R, 112 B, 120

[56] References Cited

U.S. PATENT DOCUMENTS

| 2,368,919 | 2/1945 | Fritzberg | 260/120 |
| 2,369,095 | 2/1945 | Wendt | 260/120 |
| 2,390,074 | 12/1945 | Cohn | 260/122 |
| 2,519,606 | 8/1950 | Sharp | 260/120 |
| 2,807,608 | 9/1957 | Smart | 260/120 |
| 2,897,044 | 7/1959 | Wormell | 260/123.7 |
| 2,958,628 | 11/1960 | Hink | 260/112 B |
| 3,042,526 | 7/1962 | Spiess | 34/10 |
| 3,123,593 | 3/1964 | Allan | 260/112 B |
| 3,361,732 | 1/1968 | Dazey | 260/112 B |

Primary Examiner—Paul R. Michl
Attorney, Agent, or Firm—Oblon, Fisher, Spivak, McClelland & Maier

[57] ABSTRACT

A liquid containing plasma proteins in solution and a liquid precipitant are intermixed by projecting through space a pair of convergent solid jets of respectively the solution and the precipitant so that the jets combine and the liquids thereof intermix, plasma protein being precipitated instantaneously on intermixing of the liquids and being subsequently separated from the liquid mixture; by creating miniature jets, especially jets with diameters in the range 0.5mm to 2mm, the intermixing can be effected in a small confined space whereof the temperature can be closely controlled to prevent denaturation of the mixture, intimate intermixing of the liquids can be attained practically instantaneously in said space, and jet flow can be transformed to film flow without denaturation of the mixture by foaming or turbulence.

7 Claims, 11 Drawing Figures

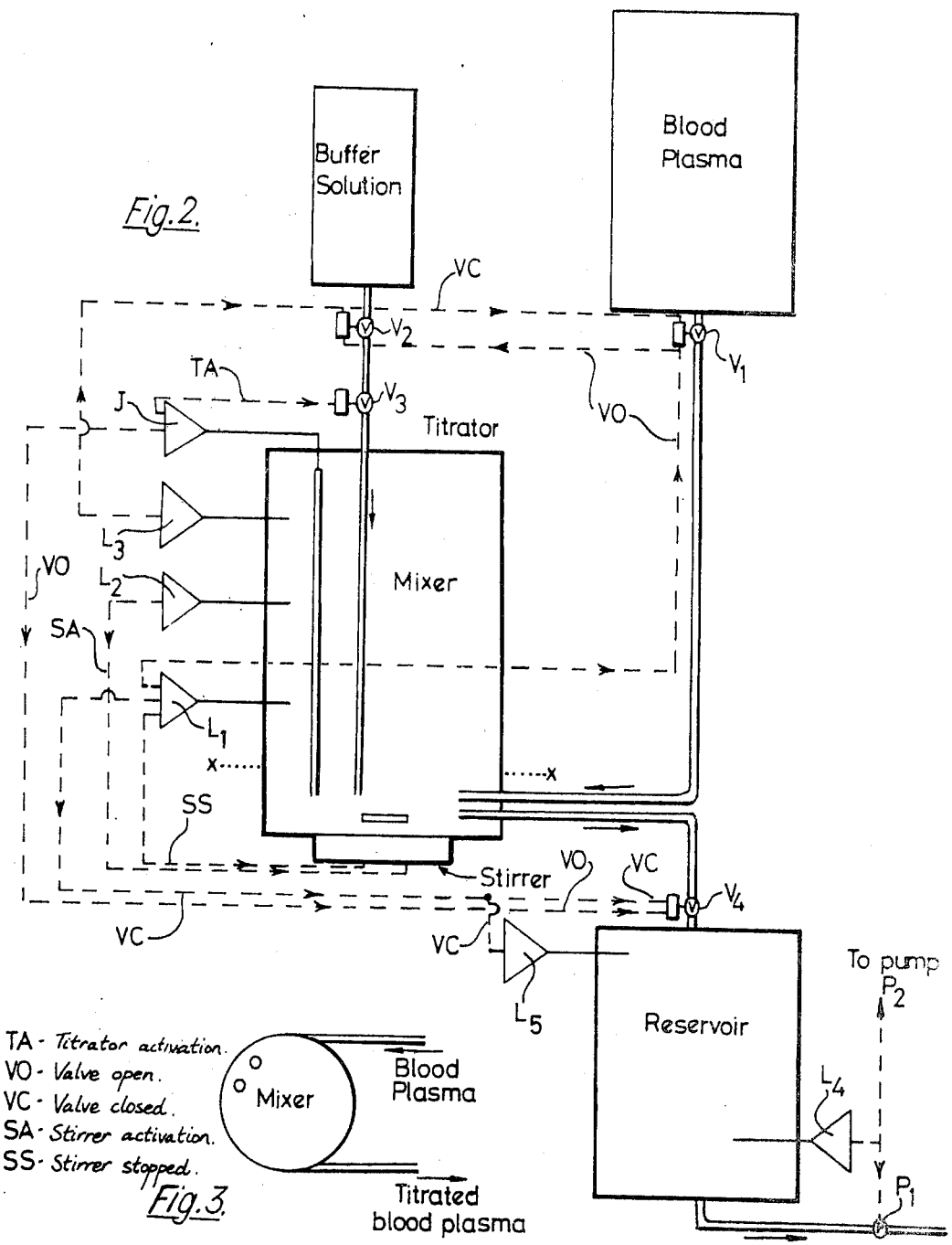

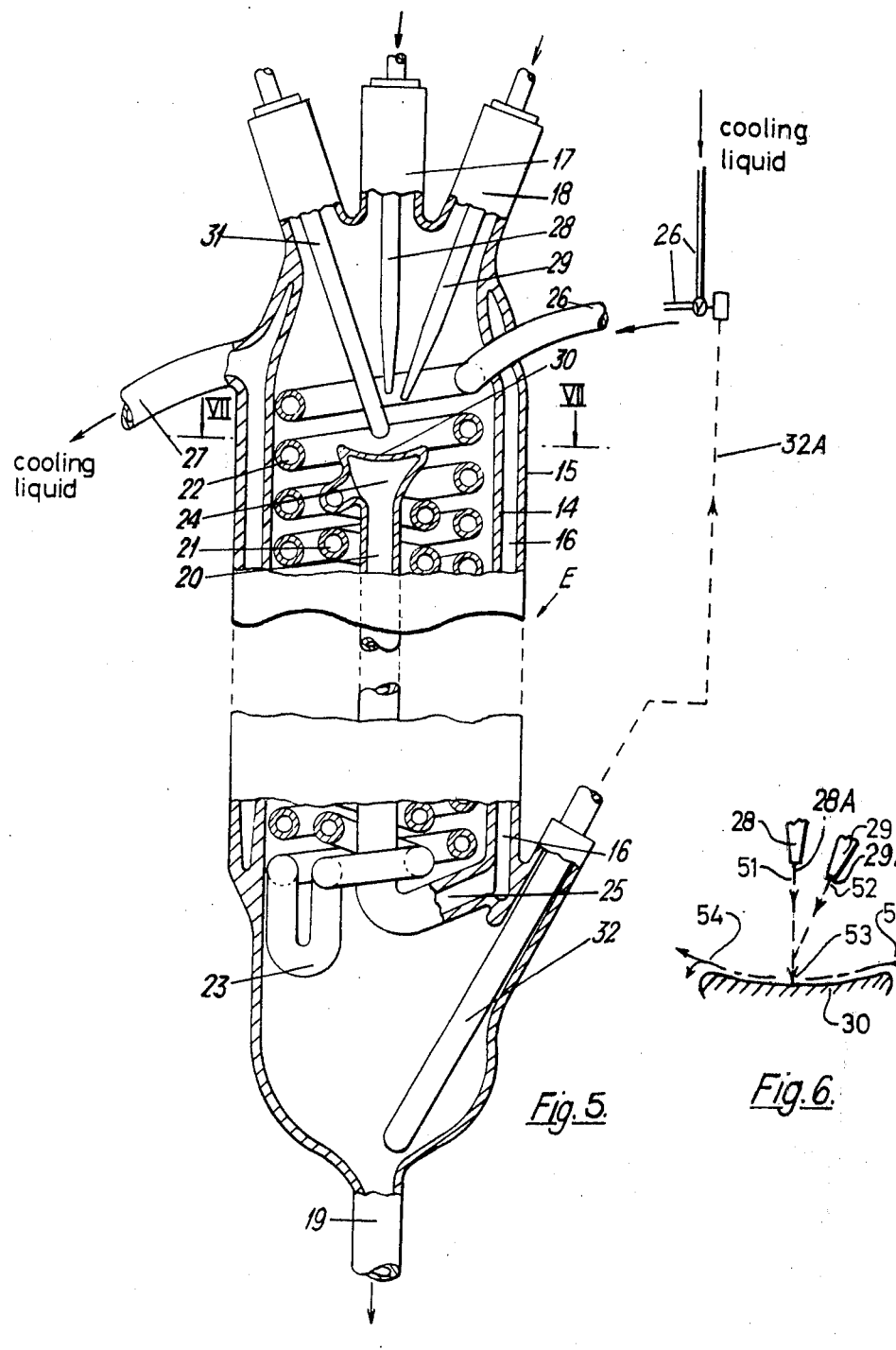

BLOOD PLASMA FRACTIONATION

This is a continuation-in-part of application Serial No. 303,761 filed Nov. 6, 1972 (now abandoned), and is concerned with an invention relating to a method of blood plasma fractionation.

BACKGROUND OF THE DISCLOSURE

It is proposed by E. J. Cohn in U.S. Pat. No. 2,390,074 that proteins useful in blood transfusion technology be produced by a blood plasma fractionation process in which an organic solvent such as alcohol is employed as a precipitant. The method proposed by Cohn depends on balancing the precipitating action of the organic solvent with the solvent actions of the electrolytes present, whereby a series of conditions may be established at which the solubility of any particular protein will remain relatively constant. The solubility of certain other proteins may in some of these conditions be such that reasonably pure separations may be possible.

In such a method five independent variables are usually controlled:
1. electrolyte concentration
2. alcohol concentration
3. hydrogen ion concentration
4. temperature
5. protein concentration Cohn teaches that when a readily denatured protein e.g. a globulin is to be precipitated, considerable care should be exercised in the addition of the precipitant to the plasma or subfraction thereof. Thus it is recommended that after suitable pH and temperature adjustment of the plasma (or subfraction thereof) the precipitant be added thereto by way of a semi-permeable membrane to avoid denaturation. It will be appreciated that the process is essentially slow and the concentration of precipitant varies continuously up to the point at which all the precipitant has been added. In consequence precipitation of fractions takes place en route and a long period of ageing is required in order to approach final equilibrium. It is in practice very rare to achieve the equilibrium condition required and the final product is almost invariably contaminated. Such bulk systems also have the disadvantage that large volumes of plasma liquor are continually at risk of plant failure or staff errors. A large ageing period has moreover been considered necessary in the past in order to achieve protein fractions having a physical form which permits ease of recovery by centrifugation, filtration or other standard methods.

Cohn also teaches that where the desired product is a less labile protein such as albumin, alternative procedures may be employed for the addition of precipitant. Plasma and precipitant may be for example supplied separately to each end of a T-shaped tube, mixing at the junction and during passage down the stem. In such a system there is however a substantial risk of obstruction by precipitated protein and the process may thereby be rendered inoperative.

SUMMARY OF THE INVENTION

It has now been found that blood plasma and subfractions thereof can be fractionated rapidly without denaturation or risk of obstruction.

Accordingly, the present invention comprises a method for the fractionation of a solution containing a plurality of plasma proteins in which spatially projected convergent jets respectively of said solution and a liquid protein precipitant are combined to form a mixture from which plasma protein is instantaneously precipitated and from which the protein is subsequently separated.

In practice the spatially projected jets are sufficiently fine that on combination the mixing is substantially instantaneous. The diameters of the outlets from which the jets are projected are typically no greater than 2mm. and desirably no smaller than 0.5mm. It is generally desirable for the jets to merge smoothly to form a composite stream which at least when the reaction between precipitant and plasma (or subfraction) is exothermic, impinges, immediately after merging, on a cooled surface so that undue rise in temperature of the mixture which is liable to cause denaturation of labile proteins therein is prevented.

The transverse dimensions of the jets and mutual orientation moreof are such that mixing is accomplished substantially without turbulence which is otherwise liable to result in denaturation and it has been found that foaming at the surface on which the jets or a composite stream formed from the jets impinge and which in undesirable for the same reason can be reduced to an insignificant level.

Usually the mixture formed by combination of the jets is immediately transformed to a film at the impingement surface, substantially without denaturing turbulence or foaming and the film is generally then subjected immediately to a further mixing action in contact with cooled surfaces. Such mixing promotes aggregation of the precipitate to facilitate eventual separation thereof, for example by centrifugation, after any further required treatment such as ageing has been conducted. Although moreover precipitation occurs instantaneously on combination of the jets, further, generally minor amounts of precipitate may be produced during the latter simultaneous mixing and cooling treatment.

The method of the present invention is particularly applicable to the precipitation from solution of plasma fractions comprising labile proteins e.g. proteins which are denatured by contact with precipitants more readily than are albumin or fibrinogen such as the globulins and especially the gamma globulins.

The precipitant may be selected from pure and mixed organic solvents, and aqueous or organic-solvent solutions of organic or inorganic precipitants, e.g. ammonium sulphate and other electrolytes. With these precipitants notably ethanol, a heating effect is obtained on dilution and in these circumstances, efficient cooling to prevent any substantial rise in the temperature of the mixture is highly important.

A process embodying the invention will now be described by way of example with reference to the accompanying drawings in which:

FIG. 2 is a schematic view of the control system of the titrating means of FIG. 1.

FIg. 3 is a sectional top plan view on the line x—x of FIG. 2.

FIG. 5 is a sectional elevation of the reaction means of FIG. 1.

FIG. 6 is an enlarged detail view of FIG. 5 showing the jet paths and liquid flow in broken lines.

Figure 1:
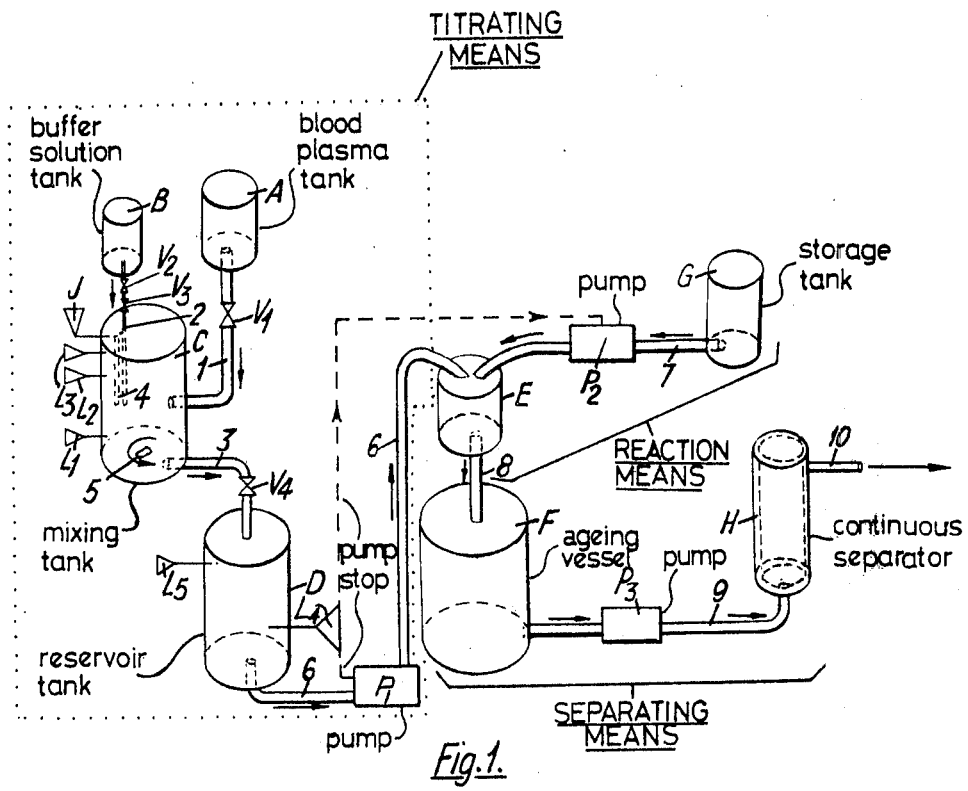
FIG. 1 is a schematic view of apparatus suitable for use in carrying out the process for the continuous fractionation of proteinaceous material and including titrating means and reaction means.

Referring to FIG. 1 of the drawing: A tank A supplies blood plasma and a tank B supplies a buffer solution. The tanks A and B are connected to a mixing tank C by lines 1 and 2 respectively. Entry valves V1 and V2 control the flow through the lines 1 and 2. C is a cylindrical, lidded, stainless vessel with a charge outlet line 3 controlled by an outlet valve V4. The tank C has the proteinaceous liquid inlet and the charge outlet disposed tangentially in the tank wall below the tank's lowermost liquid level to provide for submerged tangential inflow and outflow so that foaming of the charge in the tank is reduced. A pH sensing device or sensor unit J has its electrode 4 disposed with its tip level with the outlet end of the line 1, and the buffer entry line 2 is disposed with its outlet in the stream passing between the outlet of line 1 and the electrode tip. The unit J is a commercially available electrometric unit. Such a unit includes a Radiometer PHM26 in conjunction with a Radiometer TTT11 and provides for pH measurement in combination with an autotitrator which includes a valve V3 in the line 2 and which is accurate to within 0.05 pH units in the range of pH 4.5 to 8.5. The electrode 4 of the unit J is designed to operate at temperatures in the range $+10°$ C to $-10°$ C. The mixing tank C is mounted on a strong magnetic stirring unit 5 which includes an 80 mm. bar magnet coated with polytetrafluoroethylene and located in the vessel as a stirrer. The design of this stirring unit is such that a speed of 50–100 revolutions per minute can be continued reliably. The tank C is fitted with a series of level-sensing probes L1, L2, L3. The probes L1 and L3 are used to control the liquid valves V1, V2 and V4 which in turn control the movement of liquid into and from the tank C, the control being such that the tip of the electrode 4 is always under liquid. In use of this titrating means liquid flows by gravity from the tank A into the tank C and over the elctrode 4 of the pH sensing device J, and because of the tangential entry a rotational movement of liquid in the tank C is created. As the entry liquid bathes the electrode 4, the pH is measured; in the event of pH adjustment being required, the valve V3 of the autotitrator connected to the pH sensing device or sensor unit J operates to allow the entry of buffer liquid from the tank B to the tank C. When the C is full to the upper liquid level, probe L2 is activated to cause activation of the magnetic stirrer 5 which maintains the rotational movement of the liquid in the tank. When the required pH value is achieved ($\pm$ 0.05), the pH sensor unit J opens the valve V4 and liquid leaves the tank C through the valve-controlled line 3 until the falling level activates the probe L1 which closes the valve V4. The level of the probe L1 is so located that the electrode and the liquid inlet and outlet openings are under said level. Activation of the probe l1 is also used to stop the stirring device 5 and open the entry valves V1 and V2 to initiate the titrating cycle. The probe L3 prevents overflow by closing valves V1 and V2.

Titrated liquid leaving the tank C flows through the line 3 to a reservoir tank D.

The receiving or reaction means for the liquid reactants consists of a mixing and cooling unit E. The reservoir tank D is connected by line 6 to the unit E, and a metering pump P1 in the line 6 delivers liquid from the tank D to the unit E. A storage tank G for liquid precipitant is connected to the unit E by a line 7, and a metering pump P2 in the line 7 delivers the precipitant to the unit E. The tank D possesses liquid-level probes L4 and L5 which provide that the liquid in the tank is replenished from the tank C. In the event that there is no liquid in the tank C, the liquid level in the tank D falls to the level of the probe L4 which then stops the metering pumps P1 and P2 and so obviates the danger which would arise if the plasma pump P1 failed to pass liquid whilst the precipitant pump P2 continued to operate. The level probe L5 prevents overflow by closing the valve V4.

The cool liquid mixture discharged by the unit E runs freely downwards through a line 8.

Separating means for the cool liquid mixture from the unit E consists of a thermally insulated settling (or ageing) vessel F embodying a cooling circuit, a continuous centrifugal separator H having a discharge line 10, a line 9 connecting the vessel F with the separator H and a metering pump P3 in the line 9. The line 8 passes through the roof of the veseel F so that ejected mixture is directed against the inner aspect of the wall of the vessel such that it flows down the wall to the surface of the liquid mixture in the vessel. In this way there is little mixing of any liquid already in the vessel with the liquid entering. The vessel is provided with a flat roof which carries the probe of a capacitance level indicator (not shown) sheathed in polytetrafluoroethylene.

At the start of a mixing/cooling stage there is no liquor in the ageing vessel F, but as the mixture level rises, the ageing vessel tends to fill up. The volume of the vessel F is chosen such that the whole ageing volume can be contained in the vessel and so that the liquid level is as high as possible. Liquid is not removed from the vessel F until the mixing/cooling stage has been in operation for a period equivalent to the ageing period. At the end of this time, the liquid from the lower region of the vessel F is metered off at a rate equal to the sum of the plasma and precipitant flows, from the vessel by the pump P3 which injects the aged liquor via line 9 into the continuous separator H. At this stage the ageing vessel F contains a relatively tall cylinder of liquor aged for decreasing lengths of time according to its position in the cylinder, fully aged liquor being at the bottom and freshly added liquor at the top of the cylinder. Because of the gentle manner in which the liquor is added to the vessel there is no foaming of the added liquor and little mixing thereof with the liquor already in the vessel. By allowing the operative ageing period to be some 15 minutes longer than that considered the necessary minimum, there is no danger of inadequately aged liquor being passed to the separator H. Also, by using a relatively tall cylindrical vessel as the ageing vessel F, the slight mixing effect at the addition point is made relatively less in comparison to the full "layer" depth in the vessel. The supernatant liquid is passed from the separator H through the line 10, and may be stored for further processing to yield further fractions. The liquor entering the ageing vessel is already at the optimum precipitation temperature. While the heat insulation reduces the rate of heat input to the vessel to a relatively low level, it is insufficient to maintain complete temperature stability; the cooling circuit within the vessel ensures complete thermal stability.

The apparatus can be conveniently arranged in the form of a unit module designed to perform a particular fractionation and in practice it will be desirable to provide a number of such modules working in sequence to separate different fractions from blood or other source material.

Alternatively, the apparatus may take the form of a single mobile unit which, with its necessary supply tank, can be moved close to the site of the centrifugal separator in a refrigerated work area. In this position the apparatus is capable of adjusting the pH of the plasma to within desired limits and mixing the adjusted liquor with precipitant in optimum concentration. By adjustment of the volume and type of buffer solution employed, the apparatus is also capable of changing the ionic strength of the plasma within acceptable limits.

Figure 4:
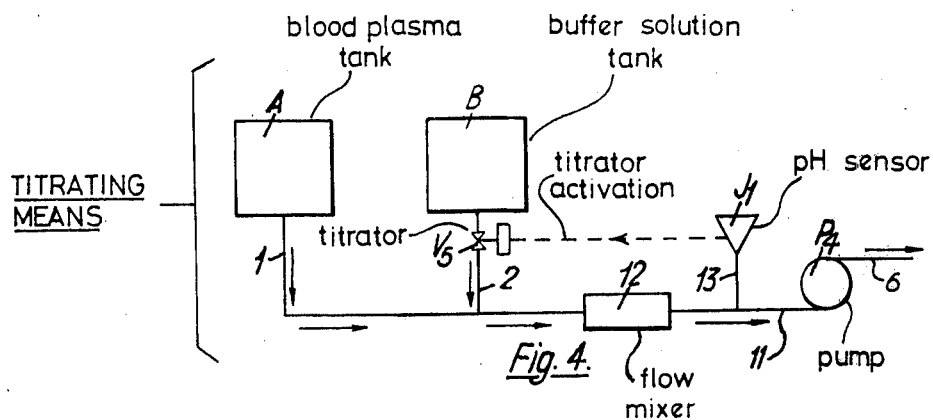
FIG. 4 is a schematic view of alternative titrating means for the apparatus of FIG. 1.

FIG. 4 is a schematic representation of alternative titrating means. The outlet lines 1 and 2 of the vessels A and B respectively discharge into a common line 11 in which there is a coiled tube 12 designed to effect mixing of the streams. The electrodes 13 of pH sensing unit J1 operatively connected to a titrator including a valve V5 in the line 2 are inserted in the line 11 near its outlet from the mixer 12. A pump P4 pressurises the liquid mixture and passes it directly through line 6 to the mixing/cooling unit E. This system of in-line mixing obviates the use of the reservoir tank D and its associated instrumentation.

The apparatus described with reference to FIGS. 1 and 2 constitutes a processing unit designed to isolate one protein fraction from the plasma. A number of such units may be interconnected to isolate a number of protein fractions from the plasma. Thus, the supernatant liquid from the line 10 may be processed or may be combined with the supernatant liquid from some other stage before being processed.

Figure 7:
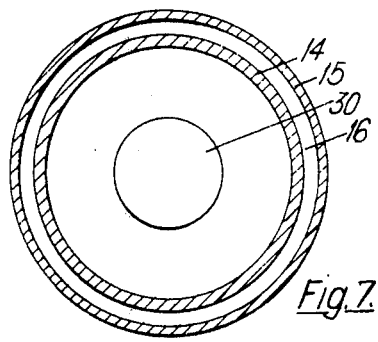
FIG. 7 is a section on the line VII—VII of FIG. 5.

In FIGS. 5 to 7 the mixing/cooling unit E of the apparatus of FIGS. 1 to 4 includes a small heat exchanger having an upright tubular vessel or casing 14, a jacket 15 for the casing forming an annular coolant space 16, and a nest of coolant tubing 20, 21, 22 in the casing which has at its upper end a pair of inlets 17 and 18 for the liquid reactants and at its lower end an outlet 19 for the liquid mixture. The coolant tubing is composed of a central upright stem 20 and inner and outer oppositely wound helical coils 21 and 22 surrounding the stem. The coils communicate with each other at their lower ends through a tube portion 23, and the upper end of the coil 21 communicates at 24 with the upper end of the stem 20 whereof the lower end communicates with the lower end of the space 16 through a tube portion 25. Liquid coolant passes into the top of coil 22 and through an inlet tube 26 and passes from the top of the jacket 15 through an outlet tube 27. The inlets 17 and 18 carry a pair of convergent nozzle tubes 28 and 29 which receive the liquid reactants from the feed lines 6 and 7 of FIG. 1 and discharge the reactants as miniature or very fine solid jets through circular nozzle orifices 28A and 29A formed at the ends of tapered nozzle portions of the tubes. The upper end of the stem 20 is enlarged to present a circular, shallowly, dished, cooled end wall 30 forming a receiver at the zone of confluence of the fine jets issuing from the nozzle orifices 28A and 29A. The orifices 28A and 29A face the receiver bottom which in spaced closely below the junction of the convergent jets issuing from the nozzles. Thermometers 31 and 32 project into the vessel respectively at the inlet and outlet ends thereof. The thermometer 32 may be a platinum resistance thermometer operatively connected through line 32A to valve means in the inlet tube 26 to effect adjustment of the temperature of the mixture leaving the vessel by causing variation of the flow of liquid coolant through the heat-exchanging ducting.

In operation of the unit E, with the liquid coolant flowing through the nest of tubing 20–22 and through the jacket 15, the very fine solid convergent jets 51 and 52 (FIG. 6) merge smoothly to form a fine, solid composite jet 53 which substantially instantly on its formation impinges on the cooling surface of the receiver 30 and instantly on impingement transforms, without substantial turbulence or foaming, into a thin, flowing film 54 of reaction mixture containing the precipitated protein fraction. That is to say, intermixture and precipitation occur instantly on impingement of the composite jet. The flow rates of the jets are such that the composite jet contains the concentration of precipitant required to precipitate the desired protein fraction. The thin film of reaction mixture containing the protein fraction as precipitate spills from the receiver 30 and flows as a film downwards over the cooling surface of the tubing 20–22 and thence through the casing's outlet 19 for collection in the ageing vessel F of FIG. 1. Control of the temperature of the mixture is effected from the instant of its formation until its discharge from the casing.

Figure 10:
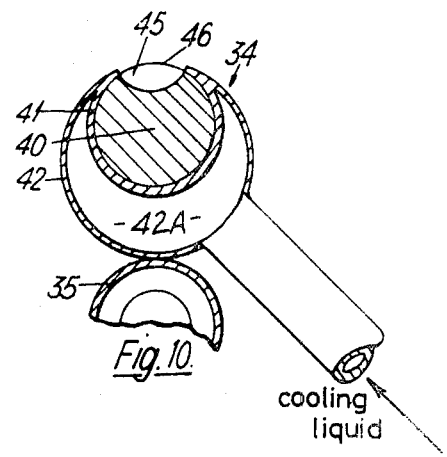
FIG. 10 is a section on the line X—X of FIG. 8.
Figure 9:
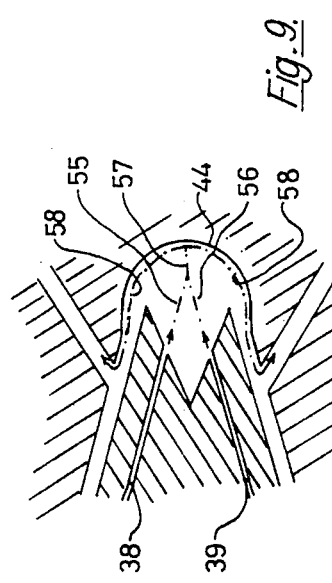
FIG. 9 is an enlarged detail view of FIG. 8 showing the jet paths and liquid flow in broken lines.
Figure 8:
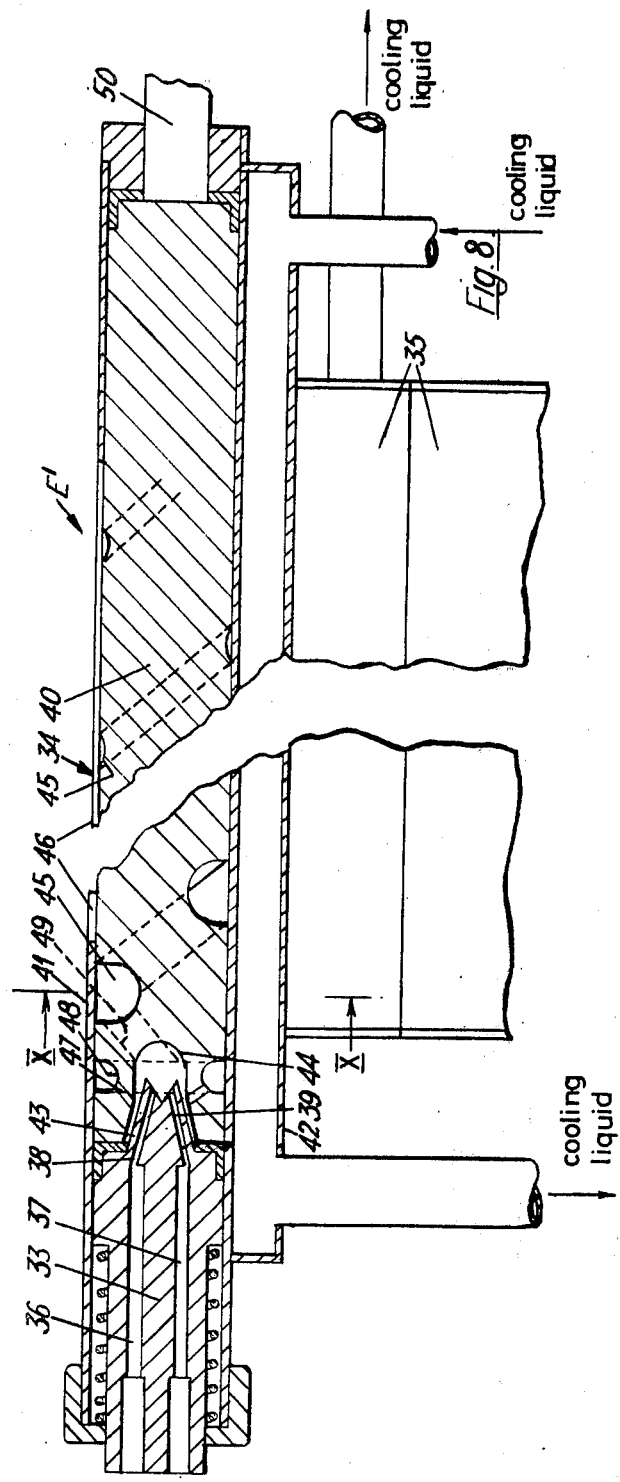
FIG. 8 is a sectional elevation of alternative reaction means for FIG. 1.

A mixing/cooling unit $E^1$ which is an alternative to the unit E of FIGS. 5 to 7 is shown in FIGS. 8 to 10. The unit comprises nozzle means in the form of a jet head 33 for the liquid reactants; and a small heat exchanger having an elongated horizontal cylindrical casing 42 for throughflow of coolant, a device in the casing for throughflow of mixture and including a cylindrical tube 41 and a helically grooved rotor 40 in the tube, and a cooler 35 of the double-walled corrugated sheet type to receive mixture from the tube 41. The jet head 33 includes a pair of parallel passages 36 and 37 which receive the liquid reactants from the feed lines 6 and 7 of FIG. 1 and communicate with a pair of convergent capillary nozzle passages 38 and 39 having diameters in the range 0.5 mm to 2 mm so as to provide circular nozzle orifices of said diameters. The rotor 40 bears on the inner end of the jet jead 33 which plugs an end of the casing 41, and a frusto-conical nose portion 43 of the jet head has the convergent nozzle passages therethrough and projects into a corresponding bore in the end of the rotor, said bore terminating in a cup-shaped receiver 44 into which the nozzle orifices discharge fine, convergent jets which have their zone of confluence at the bottom of the receiver. The outlets of the nozzle passages face the receiver wall which is closely spaced beyond the junction of the convergent jets. The rotor 40 has therein a helical groove 45 which tapers from end to end of the rotor and discharges liquid mixture through an axial slot 46 in the wall of the casing 41. A series of radial passages 47 in the rotor end connect the receiver 44 with an annular groove 48 also in the rotor end, and a passage 49 connects the annular groove with the adjacent end of the helical groove 45. The rotor is power-driven through a spindle 50 on an end of the rotor.

In operation of this unit $E^1$, the converging very fine solid jets 55 and 56 (FIG. 9) merge to form a fine, solid composite jet 57, which practically instantly on its formation impinges on the wall surface of the receiver 44, and instantly on impingement, and without substantial turbulence or foaming, is transformed into a film 58 of a reaction mixture containing the precipitated protein fraction. The amount of precipitant in the composite jet is proportioned to ensure instant precipitation of the desired protein fraction. The rotor-and-tube device in the casing is cooled by the throughflowing coolant in the casing, so that the receiver 44 presents a cooling surface on which the composite jet impinges. The mixture containing the precipitate is centrifugally discharged from the receiver 44 through the radial passages 47 and into the annular groove 48 and thence is axially fed through the tubular passage and is forcibly discharged through the slot 46 to flow as a film downwards over the cool external surface of the casing 42. The film of mixture then cascades over the cooler 35 which discharges the cooled mixture for collection in the ageing vessel F of FIG. 1. Thus, the temperature of the mixture is readily controlled from the instant of its formation until its discharge from the casing.

It is preferable that all the metering pumps used in the apparatus are gear pumps which supply a substantially pulse-free flow. The motors used are preferably air-driven in view of the fire hazard associated with the use of large amounts of ethanol as a precipitant.

The process of the invention is illustrated by the following Examples.

EXAMPLE 1

The proteinaceous material used was blood plasma isolated from blood, collected in A.C.D. solution, by centrifuging at 2,000 × g for 2 hours.

The pH of the plasma was adjusted to 7.1 10.05 in the titrating means using a 0.5M sodium bicarbonate as a buffer solution. Throughout the process the temperature was maintained at −1° C. The pH-adjusted plasma was fed at a rate of 15 liters/hour into the mixing/cooling unit along with 53.3% aqueous ethanol solution as precipitant at a rate of 2.550 liters/hour. The mixture produced was aged for 2.15 hours and then centrifuged to give a solid fraction ($F_1$) and a supernatant liquid ($S_1$).

Examples 2 to 6 are summarised in Table 1 as follows:

TABLE 1

All stages operate on the supernatant of the previous stage with the exception of Example 5 which is the precipitation of the resolubilised Fraction V + VI.

| Example No. | Fraction Isolated | Adjustment of pH | Buffer | Temp. (0° C) | Plasma flow rate (1/hr) | Ethanol flow rate (1/hr) | Conc. Ethanol Solution (%) | Ageing Time (Hrs.) |
|---|---|---|---|---|---|---|---|---|
| 2 | II + III | 6.9 ±0.05 | 0.05M Acetic Acid | −6 | 17.0 | 4.080 | 96.0 | 2.15 |
| 3 | IV | 5.85±0.05 | IM Acetic Acid | −8 | 21.0 | 5.628 | 96.0 | 2.15 |
| 4 | V + VI | 4.80±0.05 | IM Acetic Acid in 40% Ethanol | −8 | 26.2 | — | — | 2.15 |
| 5 | VI | Not adjusted 4.8 | — | −6 | 15.0 | 3.465 | 53.3 | 2.15 |
| 6 | V | 4.9 ±0.05 | 0.5M Sodium Bicarbonate | −8 | 18.2 | 9.555 | 96.0 | 2.15 |

Figure 11:
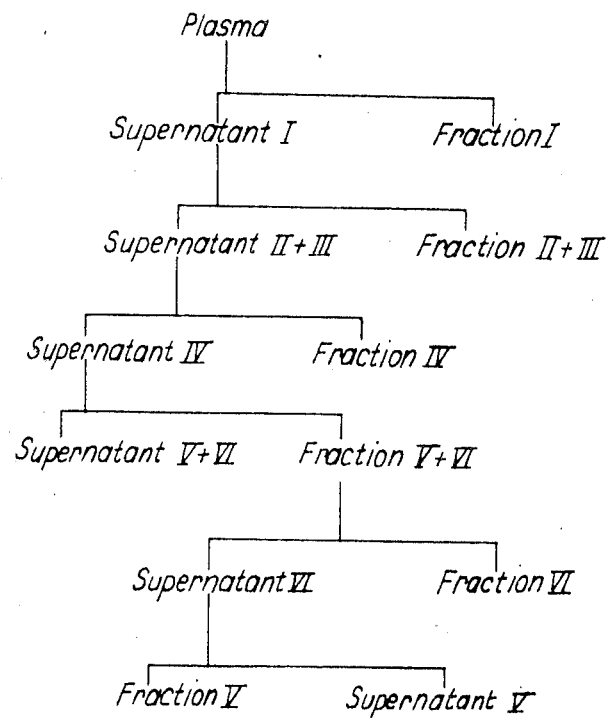
FIG. 11 is a schematic representation of the sequence of a precipitation described and exemplified in Table 1 hereinafter.

The sequence of precipitations described in the foregoing Examples is illustrated schematically in FIG. 11. Thus, the supernatant liquid ($S_1$) was processed to give a fraction $F_{II + III}$ and supernatant liquid $S_{II + III}$.

Similarly $S_{II + III}$ gave $S_{IV}$ and $F_{IV}$, $S_{II}$ gave $S_{V+VI}$ and $F_{V+VI}$. $F_{V+VI}$ was redissolved and processed to produce $F_{VI}$ and $S_{VI}$ was produced to give $F_V$ and $S_V$.

Typical analyses of the various fractions and supernatant liquids are given in Table 2 as follows:

TABLE 2

| FRACTION MATERIAL | Total Protein g/l plasma | COMPOSITION | | | | |
|---|---|---|---|---|---|---|
| | | Albumin | α-Globulins | β-Globulins | Fibrinogen | γ-Globulins |
| FRACTION I | 1.75 | 0.57 | 0.01 | 0.06 | 1.05 | 0.05 |
| SUPERNATANT I | 56.3 | 32.71 | 7.20 | 7.43 | 3.49 | 6.47 |
| FRACTION II & III | 7.17 | 0.67 | 0.52 | 1.55 | 1.38 | 3.05 |
| FRACTION IV | 7.30 | 1.30 | 2.80 | 1.90 | 0.0 | 1.30 |
| SUPERNATANT IV | 28.6 | 27.71 | 0.40 | 0.0 | 0.0 | 0.49 |
| FRACTION V & IV | 18.5 | 17.44 | 0.28 | 0.22 | 0.0 | 0.56 |
| SUPERNATANT V & VI | <1.0 | | | | | |
| FRACTION V | 16.3 | 15.56 | 0.41 | 0.33 | 0.0 | 0.0 |
| SUPERNATANT V | <1.0 | | | | | |

The particular fractionation sequence described in the Examples is only one of many possible sequences for obtaining different fractions. Also, the sequence may be extended by redissolving any of the fractions and reprocessing same to obtain a fraction of a different composition. Also, the separated supernatant liquids may be further processed either individually or in admixture one with another.

By virtue of the invention proteinaceous material may be fractioned into protein fractions containing interesting chemical entities. A general process of performing fractionation of proteinaceous material is provided and is not limited to the Examples but extends to the production of other fractions which may be isolated by judicious adjustment of the process parameters. The process has been illustrated with reference to blood plasma, but other proteinaceous material, e.g. enzyme-containing liquids, may be used equally well as starting material.

I claim:

1. A method for fractionating a solution containing a plurality of plasma proteins, which comprises: continuously converging a jet stream of a plasma containing a protein fraction to be precipitated, said fraction comprising globulin, and a jet stream of a liquid protein precipitant onto a temperature controlled surface such that admixture of said plasma and protein precipitant occurs substantially simultaneously upon impingement of said jet streams upon said temperature controlled surface so that precipitation of said protein fraction comprising globulin is initiated without significant foaming and turbulence of said mixture which denatures said protein fraction and such that when the precipitation reaction is exothermic, the resultant increase in temperature does not result in denaturation of said protein fraction; and collecting the protein fraction which precipitates from said plasma.

2. A method according to claim 1 in which said jet streams convergent are projected from outlets the diameters of which are no greater than 2mm.

3. A method according to claim 2 wherein the miniature jets are formed by nozzle orifices having diameters in the range 0.5mm to 2mm.

4. A method according to claim 1 in which the globulin is $\alpha$, $\beta$, or $\gamma$ globulin.

5. The method according to claim 1, wherein said precipitant is an electrolyte.

6. The method of claim 1, wherein said precipitant is ethanol.

7. The method of claim 1, wherein said temperature controlled surface is cooled when said precipitation reaction is exothermic.

* * * * *